United States Patent [19]

Saffran et al.

[11] Patent Number: 5,032,572

[45] Date of Patent: * Jul. 16, 1991

[54] POLYMERS CONTAINING CROSS-LINKED AZO BONDS, WHICH POLYMERS ARE USEFUL FOR RELEASING THERAPEUTIC AGENTS INTO THE LOWER GASTROINTESTINAL TRACT

[75] Inventors: Murray Saffran, Toledo; Douglas C. Neckers, Perrysburg, both of Ohio

[73] Assignees: Medical College of Ohio, Toledo; Bowling Green State University, Bowling Green, both of Ohio ; a part interest

[ * ] Notice: The portion of the term of this patent subsequent to May 5, 2004 has been disclaimed.

[21] Appl. No.: 231,491

[22] Filed: Aug. 12, 1988

Related U.S. Application Data

[60] Continuation of Ser. No. 665, Jan. 6, 1987, abandoned, which is a division of Ser. No. 631,935, Jul. 18, 1984, Pat. No. 4,663,308.

[51] Int. Cl.$^5$ .................... A61K 47/00; C07C 107/00
[52] U.S. Cl. ........................ 514/3; 514/150; 514/2; 514/54; 514/56; 514/151; 514/568; 514/772; 514/778; 514/960; 514/961; 514/962; 514/963; 514/964; 534/573; 534/843
[58] Field of Search .................. 514/3, 150, 2, 54, 56, 514/151, 568, 772, 778, 960, 961, 962, 963, 964; 534/573 P, 843

[56] References Cited

U.S. PATENT DOCUMENTS 2,784,204 3/1957 Heyna et al. ........................ 534/642
3,484,390 12/1969 Bauman et al. ...................... 514/3 X (List continued on next page.)

FOREIGN PATENT DOCUMENTS 0045006 2/1982 European Pat. Off. ................ 514/3
993961 6/1965 United Kingdom .................... 514/3

OTHER PUBLICATIONS

Peppercorn, Mark A. and Peter Goldman: The Role of Intestinal Bacteria in the Metabolism of Salicylazosulfapyridine, *J. Pharmacol. Exp. Ther.*, 181:555-562, 1972.
Saffran, M.: Oral Administration of Peptides. *Endocrinologia Experimentalis*, 16, 327-333, 1982.

*Primary Examiner*—Floyd D. Higel
*Attorney, Agent, or Firm*—Emch, Schaffer, Schaub & Porcello Co.

[57] ABSTRACT

Polymers from ethylenically unsaturated monomers, cross-linked by a substituted divinylazobenzene are useful as pharmaceutical compositions for the delivery of medicaments. The polymers are degraded by the enzymes of the upper gastrointestinal tract or are transferred intact past the upper gastrointestinal tract, to deliver the medicament to the large intestine. In particular, the polymers contain divinylazobenzene compounds of the formulae

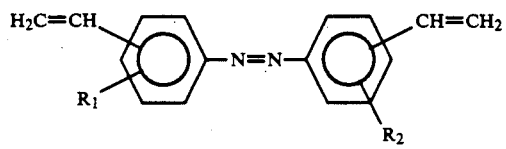

wherein $R_1$ and $R_2$ are independently selected from the group consisting of H, (except that $R_1$ and $R_2$ are not both H), Cl, Br, I, $NO_2$, $NH_2$, RO, ArO, COOH or salts thereof, COOR, COOAr, CHO, COR, $SO_3H$ or salts thereof, R or Ar and wherein R is alkyl of up to 18 carbon atoms and Ar is mono- or bicyclic aryl of up to 15 carbon atoms.

2 Claims, 3 Drawing Sheets

U.S. PATENT DOCUMENTS

| | | | |
|---|---|---|---|
| 3,780,171 | 12/1973 | Irmscher et al. | 514/3 X |
| 3,862,107 | 1/1975 | MacLeay | 534/843 X |
| 3,862,312 | 1/1975 | Rimington et al. | 514/3 X |
| 3,868,359 | 2/1975 | Sheppard et al. | 534/843 X |
| 3,976,797 | 8/1976 | Furia | 426/131 |
| 4,008,208 | 2/1977 | Lednicer et al. | 526/304 |
| 4,101,269 | 7/1978 | Champenois | 526/264 X |
| 4,129,531 | 12/1978 | Rauer et al. | 521/94 |
| 4,140,659 | 2/1979 | Clemens et al. | 521/38 |
| 4,190,716 | 2/1980 | Parkinson et al. | 525/334 |
| 4,298,595 | 11/1981 | Parkinson et al. | 514/3 X |
| 4,663,308 | 5/1987 | Saffran et al. | 514/3 |

OTHER PUBLICATIONS

Saffran, M., Franco-Saenz, R., Kong, A., Paphadjopoulous, D. & Szoka, F.: A Model for the Study of the Oral Administration of Peptide Hormones, *Can. J. Bio. Chem.*, 57, 548-553, 1979.

Arcus et al., *Index Chemicus*, vol. 16, #49093 (1965).

Davies et al., *J. Appl. Chem.*, vol. 9, pp. 368-371 (1959).

Ida et al., *J. Pharm. Soc.* Japan, vol. 89, pp. 524-530 (1969).

Kamagawa et al., *Index Chemicus*, vol. 32, #108283 (1969).

Martynoff, I, *Chemical Abstracts*, vol. 49, #8876 d,e (1955).

Martynoff, II, *Chemical Abstracts*, vol. 50, #914 d,e (1956).

Savvin et al., *Chemical Abstracts*, vol. 68, #69638K (1968).

Ueno, *J. Amer. Chem. Soc.*, vol. 79, pp. 3205-3208 (1957).

Breitenbach, *Chemical Abstracts*, vol. 42, #8521 e,f (1948).

Kurilenko et al., *Chemical Abstracts*, vol. 79, #105711 s (1973).

Shine et al., *J. Org. Chem.*, vol. 28, pp. 1232-1236 (1963).

Wiley et al., *J. Amer. Chem. Soc.*, vol. 70, pp. 2295-2296 (1948).

SMALLER TUBELET        LARGER TUBELET

1 MM

POLYMERS CONTAINING CROSS-LINKED AZO BONDS, WHICH POLYMERS ARE USEFUL FOR RELEASING THERAPEUTIC AGENTS INTO THE LOWER GASTROINTESINAL TRACT

The invention described herein was made in the course of work under a grant or award from the Department of Health and Human Services.

This application is a continuation of U.S. Ser. No. 000,665 filed Jan. 6, 1987, now abandoned, which application is a division of U.S. Ser. No. 631,935, filed July 18, 1984, now U.S. Pat. Nos. 4,663,308, issued May 5, 1987.

TECHNICAL FIELD

This invention relates to novel azo polymers, which permit site-specific delivery of therapeutic agents to or through the mucosa of the large intestine.

BACKGROUND ART

It has been proposed by Parkinson et al. in U.S. Pat. No. 4,190,716 and 4,298,595 to provide a pharmaceutical composition for the release of 5-aminosalicylic acid to the gastrointestinal tract, starting from a non-absorbable pharmacologically acceptable organic polymeric backbone, containing aromatic rings, to which are covalently bonded by azo bonds salicylic acid or salicylate salt groups. In one embodiment, polystyrene is nitrated, reduced, diazotized and coupled with salicylic acid.

In British Patent 993,961, the covalent linking of immunologically active materials, such as peptides, to polystyrene has been disclosed.

Rimington et al. (U.S. Pat. No. 3,862,312) have proposed compositions comprising acid addition salts of dl-tetramisole and a sulfonated polystyrene resin. Irmscher et al. (U.S. Pat. No. 3,780,171) have proposed ingestible polymeric compositions, in which active compounds are bound to amino-substituted polystyrenes.

Bauman et al. (U.S. Pat. No. 3,484,390) recite the formation of a diazotizable amino-function to a modified cellulosic backbone. The resulting product is a chelating resin.

Heyna et al. (U.S. Pat. No. 2,784,204) have proposed a vinylic monomer, comprising diphenylamine-vinylsulfone, which may contain azo functions and be used in dye chemistry. Furia (U.S. Pat. No. 3,976,797) indicates that polymeric azo colorants have properties, differing from those of monomeric azo colorants.

Lednicer et al. (U.S. Pat. No. 4,008,208) have proposed a pharmacologically active material, which contains azo linkages.

Peppercorn et al., *J. Pharmacol. and Infect. Therap.*, vol. 181 (1972) at 555, have described the role of intestinal bacteria in the metabolism of salicylazosulfapyridine and determined that intestinal bacteria cleave SAS to sulfapyridine and 5-aminosalicylate.

The question of the oral administration of peptides, particularly hormones, has been addressed by Saffran, *Endocrinologiea Experimentalis*, vol. 16 (1982) at 327 and by Saffran et al., *Can. J. Biochem.*, vol. 57 (1979) at 548. The use of biodegradable plastic pill coatings is considered a possible approach to solving the problem of degradation of orally-administered peptides.

It is an object of this invention to provide azo-containing polymeric materials, the azo bond of which can be degraded by chemical reduction in the large intestine of animals, including humans, to degrade the resin and permit release of medicaments to the animal. Alternatively, the resins can incorporate a medicament, which is released by reduction of the azo bonds.

DISCLOSURE OF INVENTION

In one aspect, this invention relates to a high molecular weight polymer composition, from one or more ethylenically unsaturated monomers, crosslinked by a substituted or unsubstituted divinylazobenzene.

In another aspect, this invention relates to a method for administering to an animal a medicament normally destroyed by the digestive juices of the upper gastrointestinal tract, or which must be transferred intact past the upper gastrointestinal tract or which irritates the upper gastrointestinal tract, the medicament being absorbable through the mucosa of the large intestine, or of delivering the medicament to the large intestinal mucosa of an animal requiring medicament at that location, comprising:

(a) formulating the medicament into a unit dosage form, optionally in admixture with one or more physiologically and pharmaceutically acceptable carriers, (b) coating the unit dosage form with a polymer as above, in an amount sufficient to protect the unit dosage form from the action of digestive juices of the upper gastrointestinal tract and to enable transfer of the unit dosage form intact past the upper gastrointestinal tract, and (c) administering the thus-coated unit dosage form orally to the animal being given the medicament.

This invention further relates to the improvement of encapsulating a medicament, which is unstable to the action of digestive juices of the upper gastrointestinal tract, with the foregoing polymers to accomplish administration of the medicament to the mucosa of the large intestine of an animal being treated or to permit absorption of the medicament through the mucosa of the large intestine.

In another aspect, this invention relates to high molecular weight polymers from one or more ethylenically unsaturated monomers, containing in the polymer chain a plurality of monomer units of the formula $$H_2C=CH-C_6H_4-N=N-M$$

wherein M is the residue of a medicament containing an amino group.

This invention also relates to the administration of a medicament $H_2N-M$ to or through the mucosa of the large intestine of an animal being treated, by oral administration of one of the azo polymers described above.

p,p'-Divinylazobenzene, also known as azostyrene, was made from p-nitrotoluene by the reaction sequence p-$CH_3$—$C_6H_5NO_2$ ↓ Zn, NaOH $CH_3C_6H_4-N=N-C_6H_4CH_3$ ↓ N-bromosuccimimide benzoyl peroxide $BrCH_2C_6H_4-N=N-C_6H_4CH_2Br$ -continued

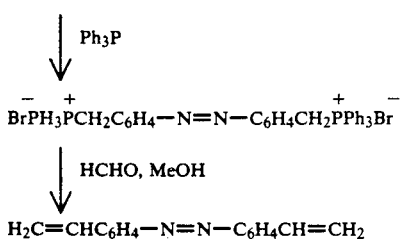

Divinylazobenzene is intended to include any of the isomeric substituted or unsubstituted compounds of the formula

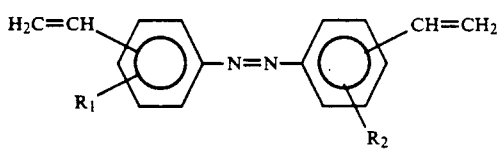

wherein $R_1$ and $R_2$ are independently selected from the group consisting of H, Cl, Br, I, $NO_2$, $NH_2$, RO, ArO, COOH or salts thereof, COOR, COOAr, CHO, COR, $SO_3H$ or salts thereof, R or Ar wherein R is alkyl of up to 18 carbon atoms and Ar is mono-or bicyclic aryl of up to 15 carbon atoms.

Any of these compounds can used as a cross-linking agent for polymers comprising units of one or more ethylenically unsaturated monomers. However, it is preferred that unsubstituted compounds ($R_1 = R_2 = H$) be used. Most preferably, the cross-linking agent is p,p'-divinylazobenzene.

Included within the class of polymers subjected to cross-linking are those containing monomer units from vinyl esters, such as vinyl acetate, vinyl propionate, vinyl butyrate, vinyl stearate and the like; acrylic esters, including methyl methacrylate, methyl acrylate, ethyl acrylate, butyl acrylate, hexyl acrylate, butyl ethacrylate, hydroxyethyl ethacrylate, hydroxyethyl methacrylate, hydroxypropyl acrylate, stearyl acrylate and the like; unsaturated acids such as acrylic acid, methacrylic acid, ethacrylic acid, crotonic acid, maleic acid and corresponding esters; acrylamide, methacrylamide; and vinylidene aromatic monomers, of which styrene, alpha-methylstyrene and the various vinyltoluenes are representative.

If desired the ethylenic monomers may be copolymerized with each other and the cross-linking agent or may be copolymerized with polyunsaturated monomers, such as butadjene or isoprene.

However, the preferred monomers for use in the practice of this invention are vinyl acetate, methyl methacrylate, styrene, acrylic acid, acrylamide, hydroxyethyl methacrylate, styrene or mixtures thereof. Most preferred are styrene and/or hydroxyethyl methacrylate.

The polymers are made by conventional methods, using known initiators such as benzoyl peroxide and azobis(isobutyronitrile).

A monomer unit of the structure $H_2C=CH-C_6H_4-N=N-M$, in the representative case in which M is salicylic acid, can be made starting from p-aminophenylethanol as follows:

$$H_2N-C_6H_4CH_2CH_2OH$$

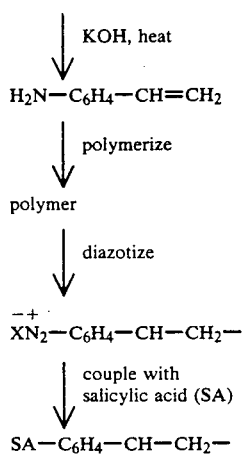

A representative vasopressin derivative, vinylphenylazo-dDAVP was made in a similar fashion.

The ethylenically unsaturated monomers, with which the vinylphenylsalicylic acid or other medicament-containing monomer can be copolymerized are as above. However, copolymers containing vinyl acetate, methyl methacrylate, acrylic acid, acrylamide, hydroxyethyl methacrylate or styrene monomers, or a combination thereof, will be preferred. It will be understood that "plurality," as applied to the monomeric units means at least about 1% of the monomeric units, depending on amount of medicament, which will ultimately be administered.

The product, wherein M was salicylic acid, could be exposed to enteric bacteria (*E. coli*) to determine whether azo reductase from the bacterial organisms would cleave the azo bonds. The reaction could be followed by a colorimetric technique to show that liberation of medicaments, bonded to azo-containing polymers, in the large intestine is feasible. In the foregoing case, the reaction can be represented by the equation:

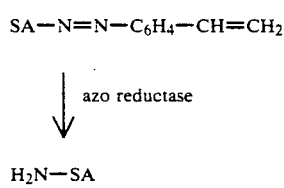

Liberation of a vasopressin derivative can be represented, in the case of dDAVP, by the equation:

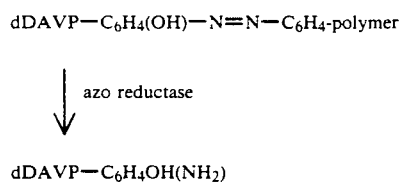

Polymers prepared in accordance with this invention can therefore be used to administer a medicament, for example, p-aminosalicylic acid, directly to the large intestinal mucosa. This provides for selective administration, of a medicament, which would normally be absorbed or destroyed in the stomach or small intestine.

Because azo bonds are stable to digestive juices in the mouth, stomach or small intestine, the polymers of this invention can be used to encapsulate and deliver medicaments which would be destroyed in the stomach or small intestine or which must be transferred intact past these organs to the large intestine, from which they can be absorbed. Typical of medicaments which can be administered in this fashion are peptide hormones, such as insulin, vasopressin or oxytocin compounds or carbohydrates, such as heparin. The azo capsules can also be used to deliver peptides such as an analog of LHRH (GnRH), which has the structure [acetyl-4-chloro-D-phenylalanyl[1], 4-chloro-D-phenylalanyl[2], D-tryptophanyl[3], D-arginyl[6], D-alanyl[10]]-GnRH HCl.

As shown in FIG. 1, dDAVP and LVP, administered in capsules coated with a polymer of this invention, induce a delayed antidiuretic response. This is consistent with the theory that the polymeric coating is not attacked until the capsule reaches the large intestine, in which the active material is released and absorbed by the intestinal mucosa.

Similar results are observed for the administration of oral vasopressin (FIG. 3), administered in azo-capsules, but not in conventionally formulated tablets.

It has also been found that $^{14}$C-salicylic acid, administered in azocapsules, appears in the urine of rats dosed therewith after a significant delay.

Therefore, the azo capsules of this invention permit delivery of a pharmacologically active agent to or through the small intestinal mucosa in a site selective fashion. It will also be appreciated that reproducibility of the delay in activity, following oral administration of a test capsule, can be used for quality control.

It is proposed that almost any drug can be delivered using an azo polymer to encapsulate the drug. For example, aspirin, which irritates and is absorbed through the mucosa of the stomach, could be delivered safely in a gel or capsule of an azo-polymer. Moreover, FDA approval of the encapsulating polymer would enable utilization of that polymer to administer any kind of therapeutic agent already known to be safe. Accordingly, use of the azo polymers, especially those cross-linked by a substituted or unsubstituted divinylazobenzene is a preferred practice of the present invention.

It is presently believed that the degradation of azo polymers in the lower intestine is brought about by the action of azo reductases as well as by the generally anaerobic conditions existing in the large intestine. Accordingly, the usefulness of materials subject to reduction in the lower intestine will be a direct function of redox potential.

It will be understood that the azo polymers can be used to encapsulate agents, intended to treat diseases and conditions of the large intestine, for example p-aminosalicylic acid, antitoxins toward E. coli toxin or other gastrointestinal toxins, and alkylating agents. It is further proposed that vaccines, which would otherwise be degraded, could be delivered in this way.

The polymers of this invention can be employed in mixtures containing conventional excipients, i.e., pharmaceutically acceptable organic or inorganic carrier substances suitable for enteral application.

Suitable pharmaceutically acceptable carriers include, but are not limited to, water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentacrythritol fatty acid esters, hydroxymethyl cellulose, poly(vinylpyrrolidone), detergents, or other adjuvants.

The preparations can be sterilized and, if desired, mixed with auxiliary agents, e.g. lubricants, stabilizers, emulsifiers, coloring agents, flavoring agents/and or aromatic substances which do not deleteriously react with the active polymers or medicaments themselves.

For enteral application, particularly suitable dosage forms are tablets, dragees, or capsules having talc and/or a carbohydrate carrier or binder or the like. The carrier is preferably lactose and/or corn starch and/or potato starch. Sustained release compositions can be formulated, including those made by varying the thickness of the polymer coating, those made by microencapsulation and those made using other types of differentially degradable coatings.

Oral administration will be preferred, for administration to animals which will not chew the azo-encapsulated medicaments. However, in experimental studies on rats, administration was done by stomach tube, which is contemplated within the scope of oral delivery.

"Upper gastrointestinal tract," as used in the specification and claims, includes the mouth, stomach and small intestine.

The compounds of this invention are generally administered to animals, particularly vertebrates, more particularly mammals, including household pets, humans, cattle, cats, and dogs.

BEST MODE FOR CARRYING OUT THE INVENTION

Figure 1:
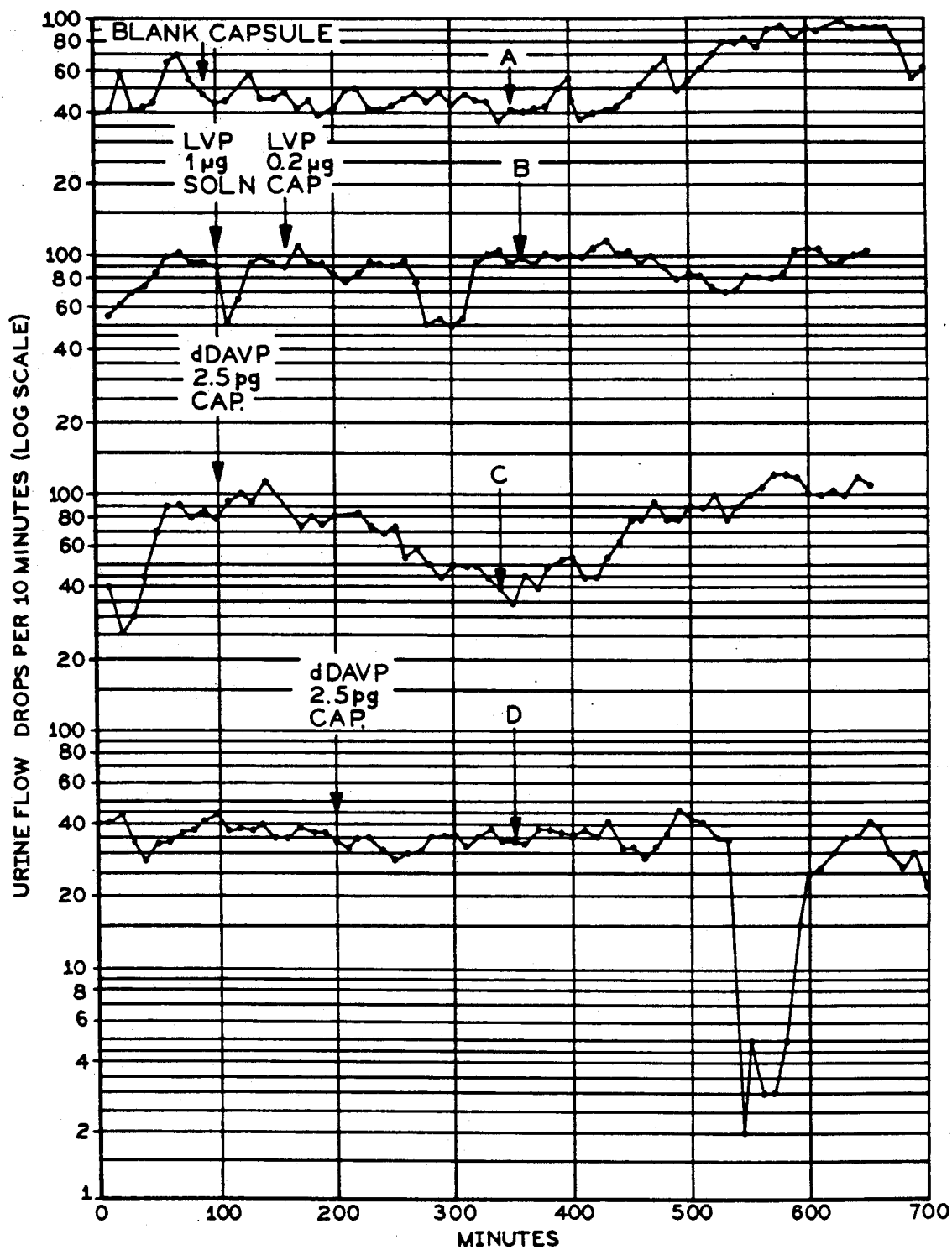
In FIG. 1 are shown effects of mode of administration of vasopressin hormones on activity as urine flow inhibitors.

Polymers cross-linked by p,p'-divinylazobenzene are preferred wherein the other ethylenically unsaturated monomer is hydroxyethyl methacrylate and/or styrene. Preferably, these polymers are used for the administration of a vasopressin compound, heparin, insulin or aminosalicylic acid.

Preferred compositions employing polymers containing

units are those where M is the residue of salicylic acid.

A preferred monomer of the formula $H_2C=CH-C_6H_4-N=N-M$ is that wherein M is salicylic acid.

Without further elaboration it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

EXAMPLE 1

(a) p-Azotoluene from p-Nitrotoluene

The synthesis was carried out according to Organic Synthesis, Coll. Vol. 3, (1955) at 103. A mixture of 109.71 g (0.8 mole) of p-nitrotoluene (0.8 mole), 1 liter of methanol, 130.0 g. (3.24 moles) of sodium hydroxide and 106.0 g. (1.64 moles) of zinc dust was stirred and heated under reflux for ten hours. The hot solution was filtered and the mother liquor was evaporated to yield orange crystals. The solid residue was extracted by stirring with acetone and removing the soluble material by decantation.

After removing acetone from the soluble material by distillation, the resulting precipitate was suspended in 2% hydrochloric acid solution, warmed, stirred and filtered. The solid product was washed with several portions of hot water and recrystallized from ethanol. The produced orange crystals were dried in a vacuum oven at 40° and melted at 134° C. (lit. trans isomer, 143.4° C.). The IR and NMR spectra were compared to Sadtler IR 13375 and NMR 7288, respectively.

(b) Preparation of p,p'-Dibromomethylazobenzene from p-Azotoluene

The procedure of *Macromolecules*, vol. 13 (1980), pages 1037–1041, was used. A mixture of 9.76 g (0.046 mole) of p-azotoluene, prepared as in Example 1(a), 18 g of N-bromosuccinimide (0.10 mole) and 0.3 g of benzoyl peroxide in 125 mL of carbon tetrachloride was heated under reflux for six hours, at the end of which a powdery precipitate had formed. Heating under reflux was continued for 6 hr, at the end of which the product was cooled and separated by filtration. The resulting mother liquor was slightly colored.

The solid product was suspended in water and filtered. The residual solid was washed several times with water or warm water and dried in air. The yield was about 16.5 g.

(c) Preparation of the Bis(triphenylphosphonium) Bromide from bis(Bromomethyl)azobenzene The product of Example 1(b) was dissolved in 400 ml of benzene (dried over calcium chloride) by stirring and heating. During the solution process, water from the wet intermediate was removed in a Dean-Stark trap.

To the thus-dried material was added triphenylphosphine (26.3 g) dissolved in benzene. The resulting mixture was heated under reflux. At the end of about an hour, an orange solid began to precipitate. Heating under reflux was continued overnight. The resulting mixture was cooled and the solid product was removed by filtration. The moter liquor was nearly colorless. The solid was washed with hexane and air dried on the filter. The yield of yellow orange precipitate was 24.7 g.

(d) Preparation of p,p'-Divinylazobenzene

The procedure was that of *Macromolecules*, vol. 13 (1980) at 1037. A mixture of 8.6 g of triphenylphosphonium bromide, prepared as in Example 1(c), 100 mL of methanol and 20 mL. of 37% aqueous formaldehyde solution was stirred and cooled in an ice bath. To the mixture was added 4N NaOH dropwise, until the appearance of a dark coloration stopped. About 40 mL of 4N NaOH were required. The product was a dark green powder, which turned orange within about 15 minutes.

The product was purified by dissolution in chloroform. The solution was dried over magnesium sulfate and filtered. Chloroform was evaporated from the dry solution and the part of the residue was dissolved in ether. The ether solution was evaporated to dryness and the residue taken up in chloroform and passed over a column of silica gel, using carbon tetrachloride as cluting solvent. The first band separated was recrystallized from ethanol and dried under vacuum, m.p. 121°–128° C.

A larger run was purified by dissolution in chloroform, drying the chloroform solution over magnesium sulfate, filtering the dried solution, evaporating the solution to a small volume and passing the solution through a 1.5 foot column packed with silica gel (carbon tetrachloride eluant). The first colored band was collected, evaporated to dryness and recrystallized from a mixture of ethanol and water.

EXAMPLE 2

(a) Vinyl Acetate Polymer Cross-linked with p,p'-Divinylazobenzene

A mixture of 10 mL of benzene (dried over calcium chloride), 5 mL of vinyl acetate, 0.05 g of p,p'-divinylazobenzene and 0.1 g of benzoyl peroxide was put in a conical flask and sparged with nitrogen, after which the flask was stoppered. During an exothermic reaction, liquid appeared to boil off. The product of the reaction was reddish brown crystals, which were washed with acetone.

The product was characterized by its IR spectrum.

(b) Vinyl Acetate Polymer Cross-linked with p,p'-Divinylazobenzene

A mixture of 5 mL of vinyl acetate, 0.05 g of benzoyl peroxide and 0.1 g of p,p'-divinylazobenzene was placed in a stoppered flask. The contents of the flask were kept at 60° C. for about three hours, at the end of which no reaction appeared to have occurred. The mixture was transferred to a tube, which was sealed and kept at 60° C. for two days. No precipitate had formed. The mixture was poured into a flask and the volatile matter was removed by distillation. The resulting product was a brown, flaky material, which was washed with acetone.

(c) Methyl Methacrylate Polymer Cross-linked with p,p'-Divinylazobenzene

A mixture of 5 mL of toluene, 5 mL of methyl methacrylate, 0.1 g of benzoyl peroxide and 0.06 g of p,p'-divinylazobenzene was placed in a glass tube. The contents of the tube were degassed under vacuum by repeated freeze-thaw cycles and the tube was scaled.

The resulting mixture was kept at 60° C. for 14 hr, at which point an orange, toluene-insoluble gel had formed. Part of the product was taken up in methanol and precipitated from methanol. The product was ground into a fine powder, which appeared to be a mixture of orange and white solids.

(d) Acrylic Acid Polymer Cross-linked with p,p'-Divinylazobenzene

A mixture of 5 mL of acrylic acid (distilled), 10 mL of absolute ethanol, 0.08 g of benzoyl peroxide and 0.05 g of p,p'-divinylazobenzene in a scaled tube were heated for 48 hr at 60° C. The yield of polymer was 0.25 g.

(e) Vinyl Acetate Polymer Cross-linked with p,p'-Divinylazobenzene

A mixture of vinyl acetate (2.5 mL), 0.025 g of 2,2'-azobisisobutyronitrile and 0.03 g of p,p'-divinylazobenzene in a screw-capped vial was heated at 60° C. for 24 hr. After removal of the liquid by distillation, the residue was stirred in methanol and filtered. About 0.1 g of reddish black powder was obtained.

(f) Acrylamide Polymer Cross-linked with p,p'-Divinylazobenzene

A mixture containing 1.8 g of acrylamide, 5 mL of benzene, 1 mL of methanol, 0.03 g of 2,2'-azobisisobutyronitrile and 0.05 g of p,p'-divinylazobenzene was heated at 55° C. for 17 hr. The mixture was bright orange at the beginning of heating, but produced a greenish yellow precipitate. The precipitate was mixed with hexane and stirred and filtered to give a yellow powder and yellow sticky polymer lumps (1.6 g).

The yellow powder was suspended in water and stirred vigorously. Part of the material dissolved; the remainder was a gel. The material was centrifuged with several portions of water to afford a precipitate. The precipitate was stirred in acetone and filtered. The product was a bright yellow powder.

(g) Acrylamide Polymer Cross-linked with p,p'-Divinylazobenzene

Mixtures similar to those of Example 2(f) were placed in screw-capped containers and heated at 56° C. for 3.5 hr, as follows:

| a | b | |
|---|---|---|
| 0.02 g | 0.02 g | 2,2'-azobisisobutyronitrile |
| 1.5 g | 1.5 g | acrylamide |
| ca 0.1% | ca.1% | p,p'-divinylazobenzene |
| (0.005 g) | (0.0453 g) | |

The yield from (a) was 0.53 g of pale yellow material and from (b) 0.10 g of bright yellow powder. The product from (a) gave a cloudy aqueous solution, which was centrifuged. An UV spectrum was obtained from the supernatant liquid.

(h) Cross-linking of Polystyrene with p,p'-Divinylazobenzene

Polymerizations were carried out as above, at 60° C. in chloroform solvent, under the following conditions:

| Run | 1 | 2 | 3 |
|---|---|---|---|
| Styrene (mL) | 2 | 2 | 2 |
| p,p'-Divinyl-azobenzene (mg) | 9 | 6 | 5.4 |
| AIBN (mole × $10^4$) | 2.3 | 3.1 | 3.5 |
| Time (hr) | 3 | 3 | 3 |
| Conversion (%) | 32.5 | 17.1 | 38.9 |
| % N | 0.51 | 0.31 | 0.31 |
| $\overline{M}_n$ | 35,000 | 32,000 | 21,000 |
| Azo (moles/L × $10^5$) | 3.45 | 2.99 | 1.20 |

(i) Cross-linking of Styrene-Hydroxyethyl Methacrylate Copolymer with p,p'-Divinylazobenzene Polymerizations were done with a monomer mixture of 3 mL of styrene and 2 mL of hydroxyethyl methacrylate at 65° C., as follows:

| Run | 1 | 2 | 3 |
|---|---|---|---|
| p,p'-Divinylazo-benzene (× $10^5$ mole) | 2.56 | 3.38 | 2.61 |
| AIBN (× $10^4$ mole) | 2.02 | 2.69 | 1.97 |
| Time (hr) | 3 | 3 | 3 |
| Conversion (%) | 18.5 | 22.0 | 25.0 |
| $\overline{M}_n$ | 25,500 | 35,360 | 18,000 |
| % N | 0.65 | 0.37 | 0.15 |

At the end of each polymerization, the viscous product was precipitated in hexane. The polymer was taken up in methylene chloride and reprecipitated. The dry product was light yellow.

Each of the samples absorbed at 360 nm and underwent cis-trans isomerization upon irradiation.

EXAMPLE 3

(a) Preparation of Hydrophilic Polymeric Film Containing p,p'-Divinylazobenzene

A mixture of 0.025 g of p,p'-divinylazobenzene, 7 mL of hydroxyethyl methacrylate, 3 mL of styrene and 0.05 g of benzoyl peroxide in methanol (20 mL) was heated under nitrogen for 1.5 hr at 55° C. The solid product was precipitated with water. The polymer was purified by dissolution in methanol and precipitation with hexane. Hexane dissolved out unreacted p,p'-divinylazobenzene. The polymer was characterized by UV and IR.

The polymer was dissolved in chloroform and used to coat gelatin capsules (Eli Lilly no. 00 and 2), filled with sand and containing a water-soluble dye. It was found that coated capsules were more resistant to the action of water, as indicated by dissolution of the water-soluble dye, than uncoated.

(b) Preparation of Poly(hydroxyethyl methacrylate) Gels Cross-linked with p,p'-Divinylazobenzene and Containing Entrapped Vasopressin A mixture of 2 mL of hydroxyethyl methacrylate, 10 mg of p,p'-divinylazobenzene, 0.05 mg of dDAVP, 2 mL of ethanol and 20 mg of 2,2'-azobisisobutyronitrile was heated at 60° C. for 5 hr in a test tube. The resulting pellet was broken into small pieces and washed with pH 7.4 buffer to remove adsorbed materials.

EXAMPLE 4

Preparation of (p-Vinylphenylazo)salicylic Acid (a) p-Aminostyrene

Dehydration of 9.2 g of p-aminophenylethanol (Chem. Abs., vol. 59:3797f) was done by heating with 8.8 g of KOH in the flame of a Bunsen burner under a nitrogen atmosphere (about 6 mm pressure). The product was collected by cooling with a Dry Ice-acetone bath. The solution was extracted with ether, dried over KOH and filtered. Evaporation of the ether gave p-aminostyrene, which was characterized by IR and NMR; the yield was 6.4 g.

Material collected from several similar runs was collected and distilled at 105° C./6 mm.

(b) Coupling of p-Aminostyrene to Salicylic Acid p-Aminostyrene (1.0 g) was diazotized with nitrous acid (from 0.58 g of sodium nitrite and 2.5 mL of concentrated sulfuric acid in 25 mL of water). The diazonium salt solution was cooled at 0°–5° C. and added to a solution of salicylic acid in dilute NaOH. After the coupling reaction, excess nitrous acid was destroyed with urea. Acidification of the resulting solution gave a greenish precipitate, which was filtered and extracted with ether. The ether extract was red brown and contained a polymeric precipitate.

The ether-soluble portions were evaporated to dryness at room temperature and were characterized by IR and NMR. The IR spectrum had both vinyl and aromatic absorption.

The product was further purfied by chromatography on a column packed with silica gel, using dichloromethane as eluant. The first fraction collected had no carbonyl absorption and was thought to be a vinylic impurity. The second fraction collected had carbonyl absorption (IR) and therefore contained the salicylic acid coupling product.

IR: 1685 cm$^{-1}$ (C=O).

UV: $\lambda_{max}$ 365, 440 nm.

The second fraction was redissolved in a small amount of methylene chloride, evaporated to a small volume and diluted with carbon tetrachloride. The resulting orange solid is mainly the coupling product of aminostyrene and salicylic acid and had a molecular weight of 268 (mass spec), as expected.

EXAMPLE 5

(a) Copolymerization of p-Vinylphenylazosalicylic Acid with Methyl Methacrylate p-Vinylphenylazosalicylic acid (0.025 g) was copolymerized with 5 mL of methyl methacrylate, using 0.1 g of benzoyl peroxide as initiator, for 2 hr at 60° C. The polymer was precipitated with methanol. The solid isolated was dissolved in chloroform and precipitated with methanol. The yield was 0.7 g of yellow polymer.

UV: $\lambda_{max}$=430 nm and 344 nm (in chloroform).

IR: 1750 cm$^{-1}$ (strong C=O stretch), shoulder 1700 cm$^{-1}$ (chloroform v chloroform).

(b) Copolymerization of p-Vinylphenylazosalicylic Acid with Styrene

A mixture of about 0.01 g of p-vinylphenylazosalicylic acid, 3 mL of styrene, about 0.05 g of benzoyl peroxide and 2 mL of chloroform was heated at 60° C. for 2 hr. The product was precipitated with methanol and isolated by filtration. The solid was reprecipitated from chloroform and methanol and weighed 0.2 g (yellow polymer). The IR spectrum of this polymer was similar to that of the product of Example 5(a).

EXAMPLE 6

Preparation of Aminosalicylic Acid Bound to Polystyrene (a) Nitration of Polystyrene Beads Polystyrene (Polysciences, Inc.; mol wt 30,000; 10 g) was stirred in 200 mL of nitration mixture (4:1 nitric:sulfuric acid v/v) in an ice-cooled bath at about 0° C. for 3 hr. The mixture was allowed to come to room temperature during 1.5 hr of additional stirring. The polymer was precipitated by pouring the nitration mixture into ice water and was removed by filtration.

The polymer was washed with several portions of water, with 5% sodium bicarbonate solution, with water and with methanol and dried in a vacuum oven at 40°. The yield was 20.2 g of bright yellow granular material.

The IR spectrum of the product showed broad absorption bands and could not be interpreted.

Anal. N: about 25%.

(b) Reduction of Nitropoystyrene to Aminopolystyrene

The procedure was that of *Chem. Abs.*, vol 66:2857 (1967).

A mixture of nitrated polystyrene (10 g), 65.5 g of stannous chloride dihydrate, 65.7 mL of HCl and 74.5 mL of ethanol was heated at 82° for 15 hr. A brown viscous layer had settled to the bottom of the reaction flask. The resulting mixture was poured into acetone, stirred and filtered. The solid product was stirred in dilute HCl and precipitated by acetone to remove most of the tin salts. The polymer was washed with sodium bicarbonate solution and with several portions of water. The weight of amorphous dark brown product was 7 g and was similar in appearance to polyaminostyrene, purchased from Polysciences. The IR spectrum was identical to that of the purchased sample (c) Diazotization Reactions with Poly(p-aminostyrene)

To a solution of 0.5 g of sulfuric acid in 10 mL of water at 0°–5° C. was added 0.2 g of poly(p-aminostyrene) (PAS). The solution was stirred vigorously at the same temperature while a solution of 0.116 g of sodium nitrite in 5 ml of water was added with continued stirring. Stirring was continued for 30 min more, whereupon excess sodium nitrite was destroyed using urea.

The solution of diazotized PAS was added slowly to a stirred solution obtained from 0.232 g of salicylic acid and 0.7 g of NaOH in 10 mL of water. During the addition, the temperature was not allowed to exceed 3°–4° and the pH of the solution was kept on the alkaline side by addition of NaOH.

After the addition was complete, the solution was stirred for half an hour. Acidification of the resulting mixture gave a brown material, appearing very similar to the starting PAS. This material was removed by filtration, washed several times with water and with acetone and dried in a vacuum oven at 40° C.

The product was difficult to characterize, but appeared to contain little coupled salicylic acid (IR) and little decrease in nitrogen content.

(d) Poly(p-aminostyrene) Diazonium Fluoroborate

PAS (0.5 g, Polysciences) was diazotized as in Example 7(c). To the diazotized solution was added a chilled solution of 1 g of sodium tetrafluoroborate in 10 mL of water. During the addition and for 15 min more, the mixture was stirred and cooled. The diazonium salt was removed by filtration and dried. The yield was 0.53 g.

UV spectra confirmed the formation of a diazonium salt:

UV (PAS): $\lambda_{max}$295 nm (DMSO)

UV (diazonium tetrafluoroborate): $\lambda_{max}$ 328 nm (DMSO).

(e) Coupling of Poly(p-aminostyrene)diazonium Fluoroborate with Salicyllic Acid

Diazonium fluoroborate (100 mg) was added to 500 mg of salicylic acid, dissolved in 1% aqueous sodium hydroxide. The resulting mixture was stirred at room temperature for 12 hr. The product which was separated was only partially soluble in DMSO. The UV spectra of the soluble fraction had a broad absorption band near 380 nm, overlapping the band at 380 nm. The newly-observed band is attributed to salicylic acid.

EXAMPLE 7

(a) Pharmacological Evaluation Protocol

Sprague-Dawley female rats, weighing about 250 g were used. The night before the experiment, food was removed from the cages. On the morning of the experiment, the rats were weighed and then given a dose of 10 mL of 15% ethanol per 250 g in warm (40° C.) water by gastric tube. The rats became comatose within 5–10 min after receiving the ethanol. Forty-five minutes later, the rats were given 2% ethanol in warm tap water at a rate of 6.25 mL/250 g.

After each rat was completely anesthesized, a catheter was introduced into the bladder and taped securely to the abdomen to prevent ejection. The rat was mounted on a modified Ohaus triple beam balance and the weights set to balance the weight of the rat plus 5–7%.

An infant feeding tube was introduced into the rat's stomach, of which the open end was attached to a plastic tube leading to a peristaltic pump, activated by a magnetic reed switch mounted on the balance. The pump was fed by a reservoir of 2% ethanol in 0.5% aqueous NaCl, kept at 40° C. As the rat lost water by urination, the weight of the rat was automatically restored with 2% ethanol solution to keep the animal anesthesized and under constant hydration. See, Sawyer, "Biologic assays for oxytocin and vasopressin," *Methods in Medical Research*, volume 9 (1961), Quastel, ed., Year Book Medical Publishers, Chicago, at 210.

The catheter from the bladder led to a drop counter, in which drops of urine interrupted an infrared beam and the resulting impulses were transformed into 5-volt pulses by a microchip circuit. The pulses were counted by a Commodore Vic-20 computer programmed to print out counts at 10-min intervals.

The agents being evaluated, e.g. vasopressin, were administered intravenously by a tail vein, subcutaneously, intraperitoneally or orally. In the latter case, the agent being evaluated was administered by the feeding tube leading to the animal's stomach. Tablets or capsules were administered by temporarily removing the feeding tube and introducing the pellet with an inserter.

Regardless of the mode of administration, urine formation was first monitored until a fairly constant flow of 30–60 drops/10 min was reached, as indicated by two or more consecutive 10-min counts being fairly constant. Sensitivity to vasopressin was determined by an oral dose of 1 μg of lysine vasopressin (LVP), given in 0.5 mL of 2% ethanol, rinsed into the stomach with 0.5 mL of 2% ethanol. As shown in FIG. 1(B) the urine flow rate decreased about 2 min after administration of LVP, reaching a minimum in 10–20 min. Urine flow returned to normal in an hour or less.

Two hours after the LVP was given, the experimental sample was administered. As shown in FIG. 1A, administration of a blank capsule, containing no vasopressin compound, resulted in practically no change in urine output during the 11-hour period of the experiment.

(b) Evaluation of Polymer-coated Capsules

Administration of LVP in a capsule, coated with a polymer of Example 2h, as shown in FIG. 1B, gave delayed inhibition of urine formation in comparison to LVP administered in the form of a solution.

Similar results were apparent from the administration of dDAVP in capsules coated with the polymer of Example 2h (FIG. 1C and 1D).

In one series of experiments, the mean response time to a solution of vasopressin (dDAVP) to maximum antidiuresis was 23.53 min ±14.53 (S.D.) and the coefficient of variation=61.8% (17 trials), whereas the mean response time to dDAVP in polymer-coated capsules was 161.5±74.58 min (S.D.) and the coefficient of variation 46.2% (20 trials).

It is therefore apparent that the polymers of this invention permit administration of active materials, absorbable through the walls of the large intestine.

(c) Evaluation of Encapsulated Vasopressin

Dried polymer of Example 3(b) was administered to rats, which underwent temporary cessation of urine formation after a delay of 30–45 min. The action was prolonged and indicates that controlled dosages of peptide hormones can be administered in polymer gels.

EXAMPLE 8

Modified Technique for Preparing and Administering Capsules

Polymer (1 g) was dissolved in 5 ml of a mixture of methanol and dichloromethane (1:4 by volume). The resulting solution was transferred to a conical polytetrafluoroethylene container with a tight-fitting polytetrafluoroethylene screw cap.

Hypodermic needles coated with a thin layer of silicone stopcock grease were used as male molds for casting tubes of the polymers. Larger diameter tubes were cast on 19 gauge needles and smaller diameter tubes on 21 gauge needles.

The silicone-coated needles were dipped twice in succession into the solution of polymer and allowed to dry in air for 30 min. The polymer tubes were removed from the needles by pushing from the hub end. Tubes slid off readily from well-lubricated needles. The tubes were set aside for 30 minutes to allow solvent to evaporate from the lumen.

The polymer tubes were cut into 3–4 mm lengths with fine sharp dissecting scissors, care being taken to keep the larger and smaller tubelets separate. One end of each tubelet was sealed by dipping the end into the polymer solution once. The dipping process was facilitated by using soft plastic tubing of proper diameter as handles. The sealed tubelets were set aside for 30 min to dry in air. The tubelets are shown, approximately to scale, in FIGS. 2A and 2B.

Powdered medicament was introduced into the smaller of a pair of tubelets, made on 21 gauge needles, by tamping the open end of the tubelet into the powder. The use of plastic tubing as a handle for the tubelet facilitated this process. The amount of powder in each tubelet was estimated by weighing the tubelet on an analytical balance before and after filling. Tubelets thus prepared hold about 1 mg of powdered sugar or medicament. Doses of medicament smaller than 1 mg can therefore be diluted with powdered sugar before filling the tubelets.

Figure 2:
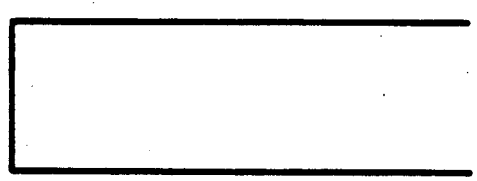
In FIG. 2 is shown the construction of azo capsules, prior to filling.
Figure 2:
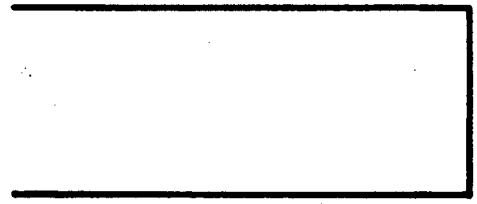
Figure 2:
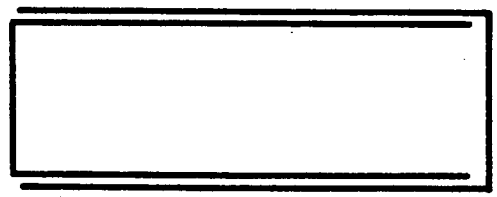
Figure 2:

Each filled tubelet was sealed by slipping the filled tubelet into the open end of a larger tubelet. This is illustrated in FIG. 2C. The resulting capsule was sealed by dipping the open end of the larger tubelet into the polymer solution and allowing the tubelet to dry in air for 30 min. The resulting capsule was ready for administration to a test animal.

Filled capsules were introduced into the stomach of rats using a 14 or 16 gauge animal feeding needle, 3 inches in length (Popper & Sons, Inc., New Hyde Park, N.Y. 11040). The ball end of the needle was dipped to a depth of 3–4 mm into a hot molten solution of gelatin (20%) and allowed to cool and harden in the refrigerator. The capsule was introduced into the hub end of the feeding needle. The feeding needle was introduced into the stomach of the rat, whereupon the capsule and gelatin seal were ejected together with a wire stylet.

EXAMPLE 9

Figure 3:
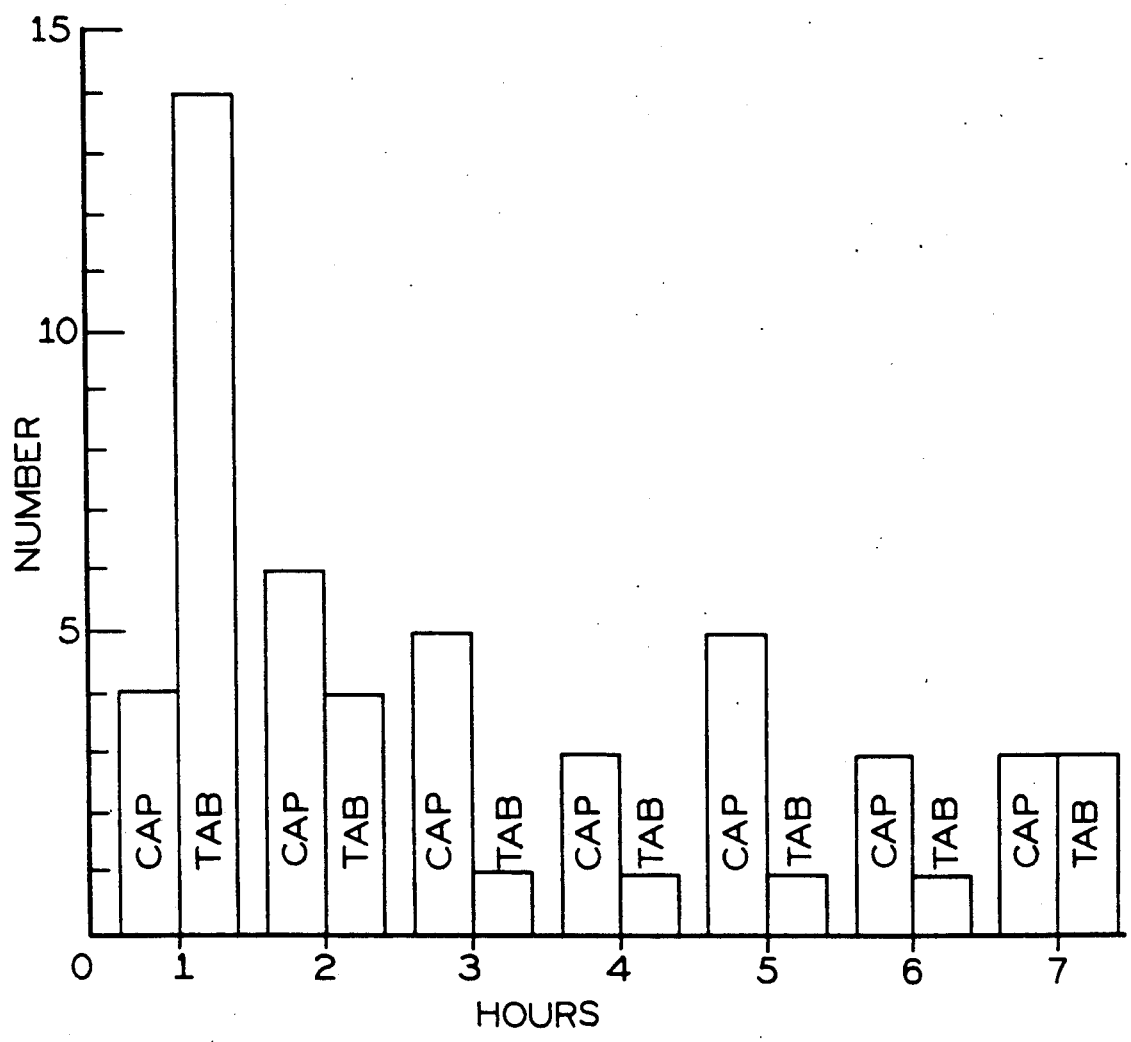
In FIG. 3 is shown the difference in antidiuretic response of rats to tablets and azo-encapsulated antidiuretic agent.

Comparison of Action of a Vasopressin Administered Orally by Tablets or by Azo-coated Capsules Capsules containing dDAVP or azo-coated capsules containing about 1 mg of dDAVP, using a 1:1 styrene-hydroxyethyl methacrylate copolymer, crosslinked with 2% by weight of p,p'-divinylazobenzene, were employed. Results are shown in FIG. 3, wherein the vertical coordinate is the frequency of peaks of antidiuresis at varying intervals after administration of conventional tablets or capsules coated in accordance with the invention.

As shown on the figure, rapid antidiuresis was observed, in most cases, following administration of tablets. However, administration of azo-coated capsules resulted in delayed onset of antidiuresis. These results are consistent with the theory that degradation of the azo polymer coating takes place in the lower intestine, rather than in the upper gastrointestinal tract. These results further indicate the feasibility of using azo capsules to administer medicaments selectively to the lower gastrointestinal tract.

EXAMPLE 10

Administration of Azo-encapsulated $^{14}$C-Salicylic Acid to Rats

The rats used for these experiments were female Sprague-Dawley rats, weighing about 250 g. The rats were fasted overnight and anesthesized with an intragastric dose of 10 ml of 15% aqueous ethanol. The anesthesia was maintained with periodic doses of 2% ethanol (0.05% NaCl in water) in an amount equal to the volume of urine lost. When urine flow was stable, as usually observed about 2.5 h after introduction of anesthesia, a capsule was introduced into the stomach of the rat by the technique described below.

The rat was located on a platform above a fraction collector. Fractions were collected at intervals of 10 or 12.5 min, depending upon the collector used. The collected urine specimens, which were of the order of 1-1.5 ml in volume, were transferred to scintillation counting vials, to each of which was added 10 ml of an aqueous counting fluid. The contents of the vials were mixed by inversion and radioactivity of the samples was determined using a Beckman scintillation counter. Five-minute counts were sufficient for the precision required.

Capsules of styrene-HEMA copolymer, crosslinked with p,p'-divinylazobenzene were prepared as in Example 8. Strips of filter papers, about 1 mm×3 mm, were placed on a polytetrafluoroethylene surface well separated from each other. Using a Hamilton syringe, 1 microliter of a solution of $^{14}$C-salicylic acid in 10% aqueous ethanol was pipetted onto each strip. The impregnated strips were allowed to dry in air for at least 30 min.

A dried paper strip was introduced into the smaller (21 gauge) azo-polymer tube and the remaining volume in the tube was filled with powdered sugar by tamping the open end of the tube into sugar. Excess sugar was wiped from the outside of the tube with paper tissue. The smaller tubelet was mated with a larger tubelet and sealed, as in Example 9. Capsules which fit a no. 16 feeding needle were used.

The tips of the feeding needles were dipped into a molten solution of gelatin (15% in water) and the needles were put in a refrigerator to harden. Just prior to use, an azo capsule containing $^{14}$C-salicylic acid, was put into the hub end of a no. 16 feeding needle. The gelatin plug prevented the capsule from falling out. The filled feeding needle was fitted onto the luer tip of a 10-ml plastic syringe. A wire stylet, fitted onto the piston of the 10-ml syringe, was introduced into the barrel of the 10-ml syringe, while holding the filled feeding needle, and into the needle itself to within 1 cm of the capsule within the needle. Capsules were introduced into the stomach of a test rat by passing the thus-prepared feeding needle down the esophagus and then into the stomach and driving the stylet into the open tip of the needle. This resulted in ejection of the capsule and gelatin plug into the stomach of the rat. The time at which the capsule was introduced was noted.

The results fell into one of three categories:

(a) No radioactivity was detected in the urine specimens for 4-8 hr. It is thought that, in these three experiments, the azo capsule remained in the stomach and did not reach the lower intestine to be degraded.

(b) Radioactivity was detected within 20-30 minutes of introduction of the capsule into the stomach of the rat. In these two cases, it is known that the capsules were damaged during introduction into the stomach. This occured upon attempted administration of two capsules through the same needle, in the lumen of which abutting ends of the capsules were crushed, so that the radioactive material leached out relatively rapidly.

(c) The first appearance of radioactive material was delayed 70-80 minutes and the radioactivity reached a plateau in about 2 hr. This occurred in three experiments and is consistent with the capsules' reaching the large intestine, where degradation of the capsule and release of radioactivity occured.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A pharmaceutical composition for the delivery of a medicament comprising (i) a divinylazobenzene compound of the formula

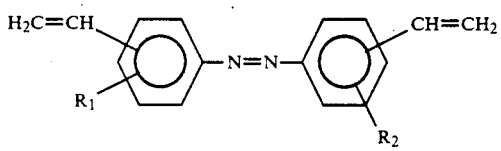

wherein $R_1$ and $R_2$ are independently selected from the group consisting of H, (except that $R_1$ and $R_2$ are not both H), Cl, Br, I, $NO_2$, $NH_2$, RO, ArO, COOH or salts thereof, COOR, COOAr, CHO, COR, $SO_3H$ or salts thereof, R or Ar and wherein R is alkyl of up to 18 carbon atoms and Ar is mono- or bicyclic aryl of up to 15 carbon atoms, the divinylazobenzene compound being copolymerized with one or more ethylenically unsaturated monomers to produce a polymer useful as carriers or capsules to deliver to the large intestine of an animal the medicament having an undesired effect on the upper gastrointestinal tract or being absorbed therethrough, which medicament is capable of being absorbed through the mucosa of the large intestine or of acting directly in the large intestine; and (ii) at least one pharmaceutically acceptable excipient.

2. A pharmaceutical composition for the delivery of a medicament comprising:

(i) a divinylazobenzene compound of the formula

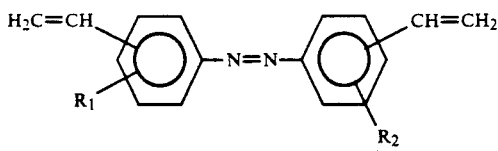

wherein $R_1$ and $R_2$ are independently selected from the group consisting of H, (except that $R_1$ and $R_2$ are not both H), Cl, Br, I, $NO_2$, RO, ArO, COOH or salts thereof, COOR, COOAr, CHO, COR, $SO_3H$ or salts thereof, R or Ar and wherein R is alkyl of up to 18 carbon atoms and Ar is mono- or bicyclic aryl of up to 15 carbon atoms, the divinylazobenzene compound being copolymerized with one or more ethylenically unsaturated monomers to produce a polymer; and (ii) at least one pharmaceutically acceptable excipient.

* * * * *